United States Patent
Hata et al.

(10) Patent No.: US 10,085,790 B2
(45) Date of Patent: Oct. 2, 2018

(54) LUNG VOLUME REDUCTION METHOD

(71) Applicant: TERUMO KABUSHIKI KAISHA, Tokyo (JP)

(72) Inventors: Suguru Hata, Kanagawa (JP); Ayaka Akutagawa, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 733 days.

(21) Appl. No.: 14/463,607

(22) Filed: Aug. 19, 2014

(65) Prior Publication Data
US 2015/0051596 A1 Feb. 19, 2015

(30) Foreign Application Priority Data
Aug. 19, 2013 (JP) .................. 2013-169944

(51) Int. Cl.
*A61B 18/04* (2006.01)
*A61B 18/02* (2006.01)
*A61B 18/00* (2006.01)

(52) U.S. Cl.
CPC .............. *A61B 18/04* (2013.01); *A61B 18/02* (2013.01); *A61B 2018/00541* (2013.01); *A61B 2018/00595* (2013.01)

(58) Field of Classification Search
CPC .................. A61B 18/02; A61B 18/04; A61B 2018/00541; A61B 2018/00595
See application file for complete search history.

(56) References Cited

U.S. PATENT DOCUMENTS

| | | | | |
|---|---|---|---|---|
| 5,690,675 A | * | 11/1997 | Sawyer | A61B 17/00491 128/898 |
| 6,003,517 A | * | 12/1999 | Sheffield | A61B 18/1447 128/898 |
| 6,493,589 B1 | * | 12/2002 | Medhkour | A61B 18/1492 604/114 |
| 2003/0018327 A1 | * | 1/2003 | Truckai | A61B 18/1492 606/32 |
| 2003/0228344 A1 | * | 12/2003 | Fields | A61F 2/04 424/423 |
| 2006/0161233 A1 | * | 7/2006 | Barry | A61B 18/04 607/113 |
| 2008/0097139 A1 | * | 4/2008 | Clerc | A61B 18/0218 600/7 |
| 2009/0143705 A1 | * | 6/2009 | Danek | A61B 18/08 601/3 |
| 2010/0256713 A1 | * | 10/2010 | Edwards | A61B 1/00082 607/105 |

* cited by examiner

*Primary Examiner* — Daniel Fowler (57) ABSTRACT

A treatment method is provided which exhibits a reliable therapeutic effect on chronic obstructive pulmonary disease. In the treatment method, lung volume is reduced by restraining expansion and contraction of lung parenchyma present in the vicinity of a verge of a lung having an emphysema-suffering part, at least in one site of the verge.

13 Claims, 9 Drawing Sheets

LUNG VOLUME REDUCTION METHOD

CROSS REFERENCE TO RELATED APPLICATION

This application is based on Japanese Application No. 2013-169944, filed on Aug. 19, 2013, the contents of which are incorporated herein by reference.

BACKGROUND

The present disclosure relates to a method for the reduction of lung volume.

Chronic obstructive pulmonary disease (COPD) means a wide variety of lung diseases that hinder normal breathing, and is a disease of lung obstruction caused by pulmonary emphysema or chronic bronchitis.

Of these diseases, the pulmonary emphysema refers to a state of abnormal enlargement with destruction of tissues called pulmonary alveolar parenchyma inclusive of respiratory bronchioles, alveolar duct, pulmonary alveoli and alveolar sacs serving as sites of gas exchange. Although the pulmonary alveolar parenchyma in its normal state shrinks at the time of expiration, emphysema-suffering pulmonary alveolar parenchyma does not return into its original state if once enlarged by breathing. Therefore, sufficient breathing is not possible. Moreover, an effective area and vascular bed (blood capillaries running in various directions on the surfaces of the pulmonary alveoli) of the pulmonary alveoli decrease, thereby lowering the ventilatory capacity of the lungs as a whole. In addition, since elastin and the like are destroyed due to inflammation, the elasticity of the lung is lowered and it is not possible to keep stretching and expanding the respiratory tract. The result is a state permitting easy deformation of the bronchi. Accordingly, as the lungs contract at the time of expiration, the bronchi thereof are narrowed by being compressed with the surrounding air-filled pulmonary alveoli, resulting in that the lungs are hyperinflated, making it difficult to release the air.

As a treatment of pulmonary emphysema, at present, lung volume reduction surgery (LVRS) in which the lesion part of the lung is removed so as to promote expansion of normal lung parts is adopted as a surgical method, in addition to the oxygen therapy and pharmacotherapy which alleviate the symptom of the disease on a temporary basis. In the lung volume reduction surgery, however, not only the lesion part of the lung but also much normal part in the vicinity of the lesion part may be removed. In addition, the surgery is highly invasive, and the patient must be kept hospitalized for a long time. Thus, this surgical therapy imposes a great burden on the patient.

On the other hand, Japanese Publication No. JP2012/501813 proposes a therapeutic method for mitigating a hyperinflation state of lung by shrinking the lung, without removing the lesion part of the lung. In this therapeutic method, a shape memory alloy coil having undergone such shaping as to rake up the surrounding tissues is set indwelling in the lung parenchyma such as a bronchus having an emphysema-suffering part, and the tissues in the surroundings of the bronchus are raked up together with the bronchus, thereby shrinking the lung as a whole. Furthermore, by utilizing the elasticity possessed by the coil, tension is imparted to the fiberized lung, so as to assist the shrinkage of the lung at the time of expiration, thereby ensuring easy release of the air from the lung.

SUMMARY OF THE DISCLOSURE

According to the just-mentioned method, the hyperinflated state of the lung can be mitigated, and the shrinkage of the lung at the time of expiration can be assisted. Therefore, a certain degree of therapeutic effect can be obtained. This method, however, cannot be applied to such a patient in whom the tissues to be raked up have been lost in the lung parenchyma and the surroundings due to the progress of the emphysema. Therefore, the candidate patients for application of this therapeutic method would be limited depending on the symptom of the affected part (lesion part). Thus, this method lacks versatility.

In view of the foregoing, it is an intention of the present disclosure to provide a treatment method which exhibits a reliable therapeutic effect on chronic obstructive pulmonary disease.

This treatment method can be attained by any of the following embodiments of the disclosed methods.

In a first embodiment, method is disclosed for reduction of lung volume, including restraining expansion and contraction of lung parenchyma present in a vicinity of a verge of a lung having an emphysema-suffering part, the restraining performed at least in one site of the verge, thereby to reduce the lung volume.

The restraining of the expansion and contraction of the lung parenchyma as described in accordance with this first embodiment is conducted at least at a lobe having the emphysema-suffering part, of lobes included in the lung, and the restraining of the expansion and contraction of the lung parenchyma is conducted in a predetermined range including at least one of margo inferior, horizontal fissure, oblique fissure, diaphragmatic surface, apex of lung, anterior margin, cardiac notch, and lingula, of the verge of the lung. Further, the restraining of the expansion and contraction of the lung parenchyma is conducted at least in a continuous region of the predetermined range.

This restraining of the expansion and contraction of the lung parenchyma is conducted at least at a plurality of parts in the predetermined range, and may be conducted in a spot-like pattern and/or in a linear pattern extending to the verge, at a part other than the verge.

In another embodiment, the method for the reduction of lung volume comprises a reduced-elasticity part where elasticity of the lung parenchyma is reduced is formed in the lung in order to restrain the expansion and contraction of the lung parenchyma. The reduced-elasticity part is formed by at least cauterizing living-body tissue of the lung. Alternatively, the reduced-elasticity part is formed by at least fiberizing living-body tissue of the lung. The reduced-elasticity party may also be formed at least by hardening living-body tissue of the lung, or at least cooling living-body tissue of the lung.

In still another embodiment, the method for reduction of lung volume includes a constraining instrument for constraining living-body tissue of the lung is at least used in order to restrain the expansion and contraction of the lung parenchyma. This restraining of the expansion and contraction of the lung parenchyma may be conducted by use of a medical device introduced transbronchially and/or a medical device introduced from a body surface side.

According to the aspect of the present disclosure as described, it is possible to reduce the volume of the lung having an emphysema-suffering part, and to alleviate the feeling of difficulty in breathing. Therefore, it is possible to exhibit a reliable therapeutic effect on chronic obstructive pulmonary disease.

According to the aspect of the disclosure as described, the restraining of the expansion and contraction of the lung parenchyma is conducted at least in the lobe having an emphysema-suffering part, of the lobes included in the lung. Therefore, lung volume can be reduced more suitably.

According to the aspect of the disclosure as described, the restraining of the expansion and contraction of the lung parenchyma is conducted in a predetermined range including at least one of margo inferior, horizontal fissure, oblique fissure, diaphragmatic surface, apex of lung, anterior margin, cardiac notch, and lingula, of the verge of the lung. Therefore, it is possible to restrain a downwardly dilating action of the lung and, hence, to prevent favorably the inflow of gas into the inside of the lung.

According to the aspect of the disclosure as described, the restraining of the expansion and contraction of the lung parenchyma is conducted at least in a continuous region of the predetermined range. Therefore, it is possible to restrain the dilating action of the lung more favorably, and to reliably reduce the lung volume.

According to the aspect of the disclosure as described, the restraining of the expansion and contraction of the lung parenchyma is conducted at least at a plurality of parts in the predetermined range. Therefore, it is possible to restrain the dilating action of the lung further suitably, and to reliably reduce the lung volume.

According to the aspect of the disclosure as described, the restraining of the expansion and contraction of the lung parenchyma is conducted in a spot-like pattern and/or in a linear pattern extending to the verge, at a part other than the verge. Therefore, the lung volume can be reduced efficiently.

According to the aspect of the disclosure as described in the above paragraph, a reduced-elasticity part where elasticity of the lung parenchyma is reduced is formed in the lung in order to restrain the expansion and contraction of the lung parenchyma. Therefore, the expansion and contraction of the lung parenchyma can be restrained in a sustained manner.

According to the aspect of the disclosure as described, the reduced-elasticity part is formed by cauterizing living-body tissue of the lung. Therefore, it is possible to restrain the expansion and contraction of the lung parenchyma more reliably.

According to the aspect of the disclosure as described, the reduced-elasticity part is formed by fiberizing living-body tissue of the lung. Therefore, it is possible to restrain the expansion and contraction of the lung parenchyma more reliably.

According to the aspect of the disclosure as described, the reduced-elasticity part is formed by hardening living-body tissue of the lung. Therefore, it is possible to restrain the expansion and contraction of the lung parenchyma more reliably.

According to the aspect of the disclosure as described, the necrosis is induced and the reduced-elasticity part is formed by cooling living-body tissue of the lung. Therefore, the expansion and contraction of the lung parenchyma can be restrained further reliably.

According to the aspect of the disclosure as described, a constraining instrument for constraining living-body tissue of the lung is used in order to restrain the expansion and contraction of the lung parenchyma. Therefore, the restraining of the expansion and contraction of the lung parenchyma and removal of the restraint can be performed in a reversible manner.

According to the aspect of the disclosure as described, the restraining of the expansion and contraction of the lung parenchyma is conducted by use of a medical device introduced transbronchially and/or a medical device introduced from a body surface side. Therefore, an introducing method promising easier access can be arbitrarily selected according to the part to be treated and the kind of the medical device, and the treatment can be carried out speedily and easily.

BRIEF DESCRIPTION OF THE FIGURES

FIGS. 1A and 1B illustrate a lung to which a lung volume reduction method according to an embodiment of the present disclosure has been applied, wherein

FIGS. 2A and 2B illustrate the lung to which the lung volume reduction method according to the embodiment of the present disclosure has been applied, wherein

FIGS. 3A and 3B illustrate the lung to which the lung volume reduction method according to the embodiment of the present disclosure has been applied, wherein

FIGS. 4A and 4B illustrate the conceptual principle of reduction of lung volume by restraining the expansion and contraction of lung parenchyma present in the vicinity of the verge of a lung, wherein

FIGS. 5A and 5B illustrate a procedure for treating the verge of a lung, wherein

DETAILED DESCRIPTION OF THE DISCLOSURE

An embodiment of the present disclosure is described herein in connection with the figures. The dimensional ratios in the drawings may be exaggerated for convenience of description and may, therefore, be different from the actual ratios.

Figure 4A:
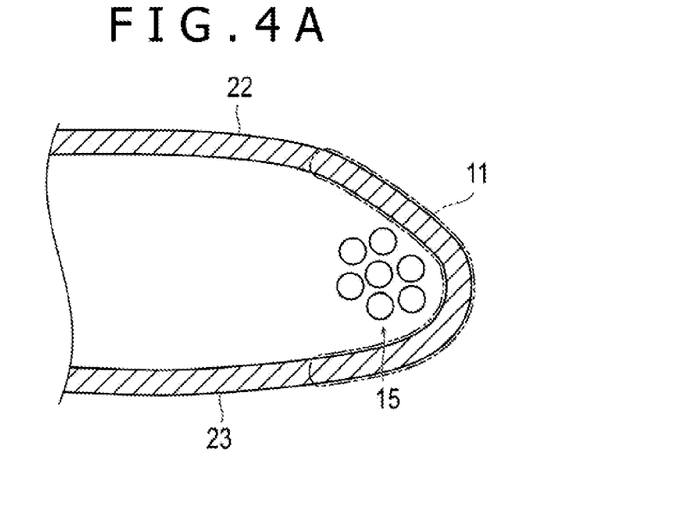
FIG. 4A is a sectional view showing in a magnified form a part of the verge in the state before the restraint of the expansion and contraction of the lung parenchyma.
Figure 4B:
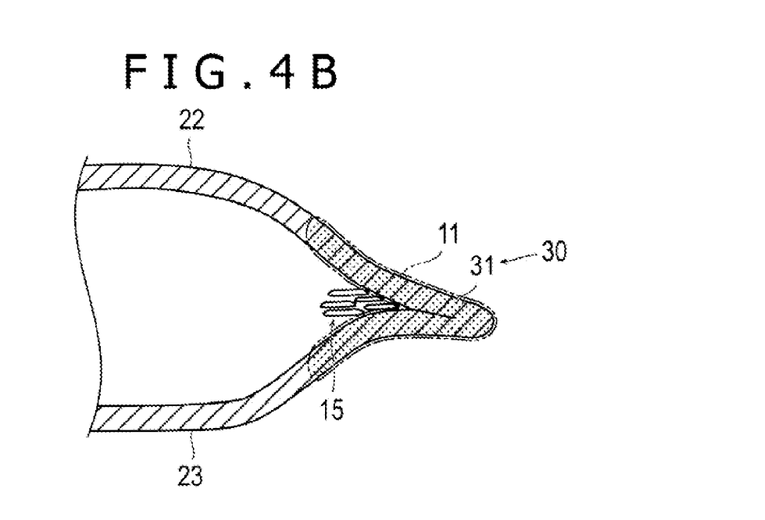
FIG. 4B is a sectional view showing in a magnified form a part of the verge in the state where the expansion and contraction of the lung parenchyma are restrained.
Figure 5A:
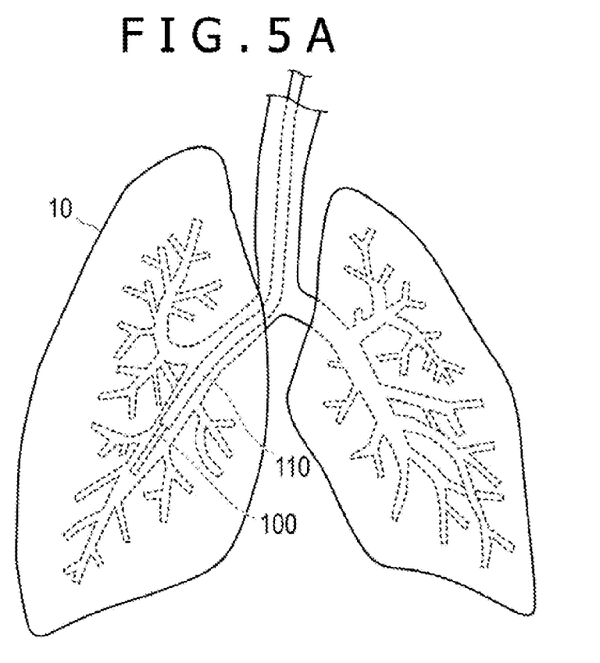
FIG. 5A is a schematic illustration of a procedure for introducing a medical device in a transbronchial manner.
Figure 5B:
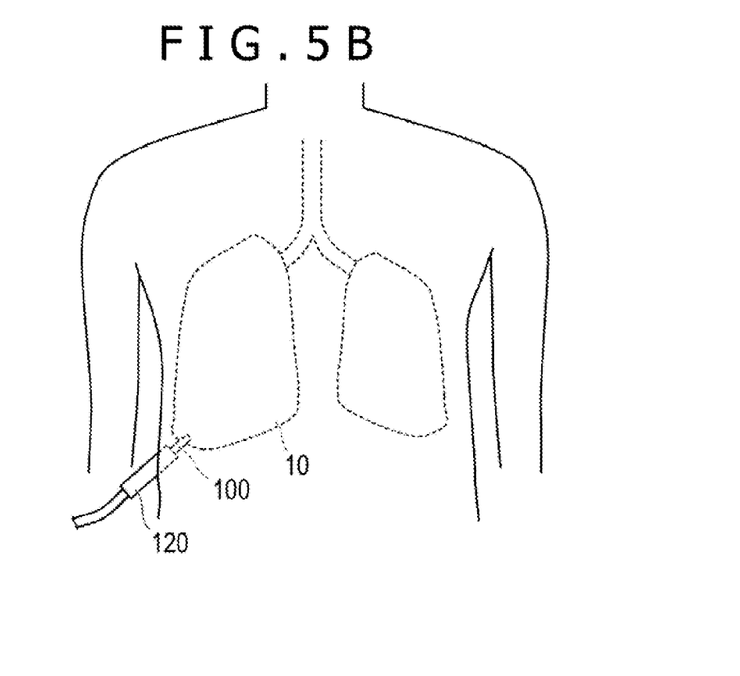
FIG. 5B is a schematic illustration of a procedure for introducing a medical device in a percutaneous manner through a body surface.

FIGS. 1A to 3B illustrate a lung to which the lung volume reduction method according to the present disclosure has been applied. FIGS. 4A and 4B illustrate the principle of reduction of lung volume. FIGS. 5A and 5B are drawings for illustrating a procedure for lung volume reduction. In the figures, an X-axis represents the width direction of the lung, a Y-axis the longitudinal direction of the lung, and a Z-axis the thickness direction of the lung.

The lung volume reduction method (hereinafter referred to also as "the treatment method") according to this embodiment is a method wherein the volume of a lung having an emphysema-suffering part is reduced so as to mitigate a hyperinflated state of the lung, whereby the symptom of the pulmonary emphysema disease can be alleviated.

Figure 1A:
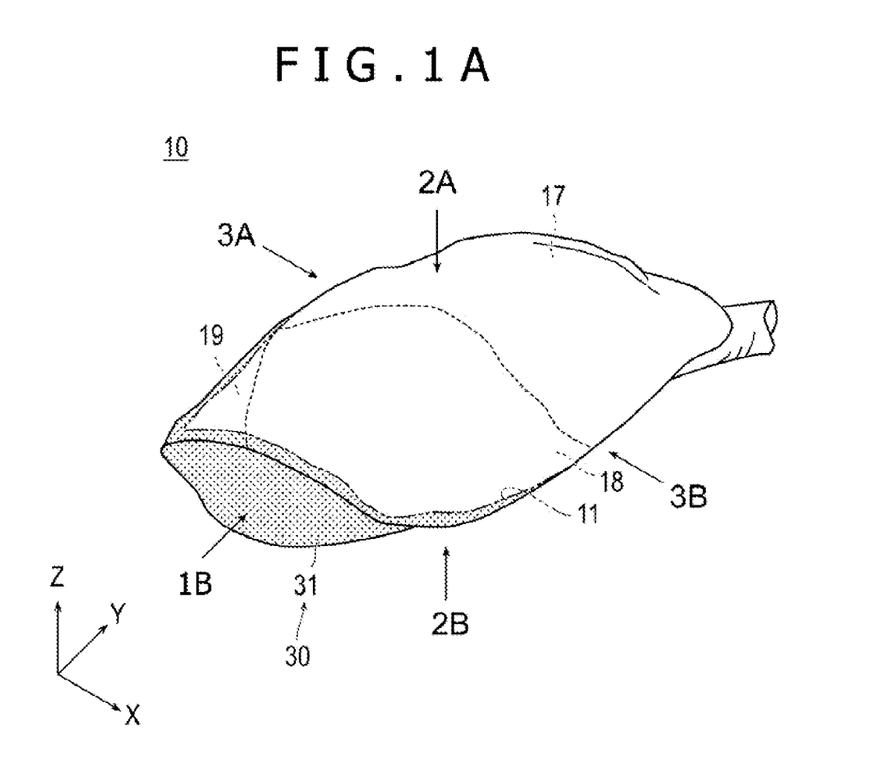
FIG. 1A is a schematic perspective view of the lung.
Figure 1B:
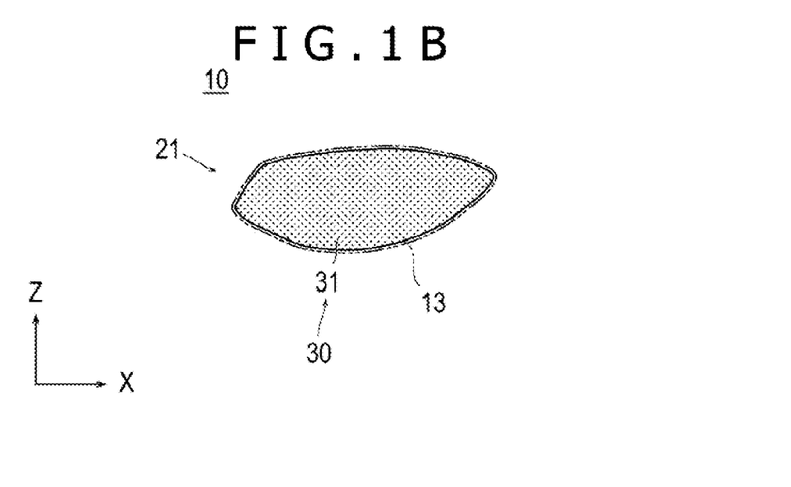
FIG. 1B is a view showing a bottom surface of the lung as viewed along arrow 1B in FIG. 1A.
Figure 2A:
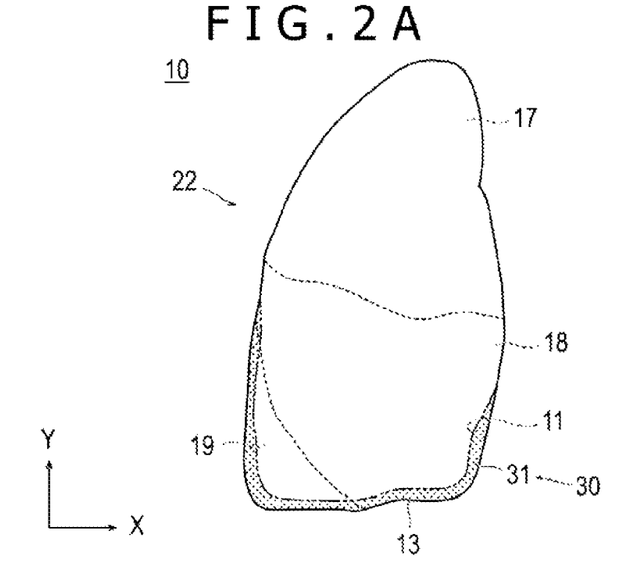
FIG. 2A is a view showing a front surface of the lung as viewed along arrow 2A in FIG. 1A.
Figure 2B:
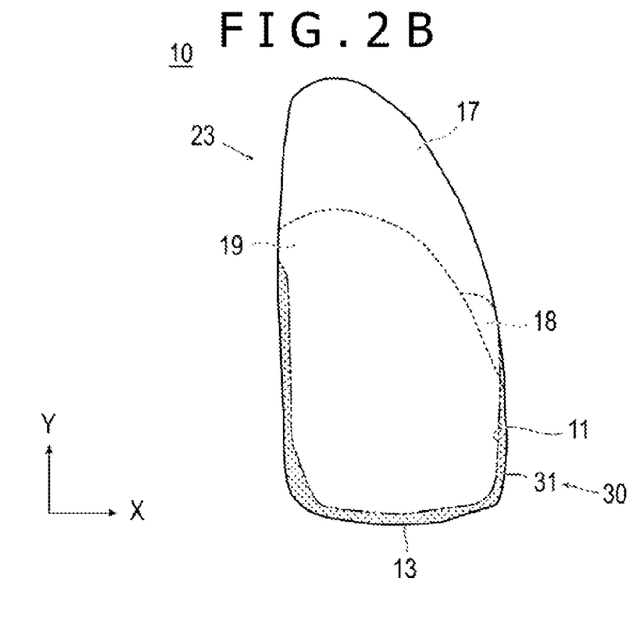
FIG. 2B is a view showing a back surface of the lung as viewed along arrow 2B in FIG. 1A.

As shown in FIG. 1A, the treatment method according to this embodiment includes restraining the expansion and contraction of lung parenchyma 15 (see FIG. 4A) present in the vicinity of a verge 11 of a lung 10 having an emphysema-suffering part, such that the restraining is conducted in at least one site of the verge 11. In FIGS. 1A to 3B, the boundary of the verge 11 is indicated by the two-dot chain line. The expression "the verge of the lung" means a certain part inclusive of a boundary portion (ridge line portion) of an outer circumferential edge forming the external shape of the lung 10. The part where restraining the expansion and contraction of the lung parenchyma 15 occurs may be any site or range that is part of the verge 11 of the lung 10. In the present embodiment, the range surrounded by the two-dot chain line (the part which is dotted in the drawings, and which corresponds to the "reduced-elasticity part 31" to be described later) is set to be a target part 30 to be treated.

With reference to FIGS. 4A and 4B, the principle of lung volume reduction by restraining the expansion and contraction of the lung parenchyma 15 present in the vicinity of the verge 11 of the lung will now be described.

Referring to FIG. 4A, the lung parenchyma 15 (alveolar epithelial cells and the alveolar space surrounded thereby) has the function as a site of gas exchange through which oxygen is taken into the inside of the body and carbon dioxide (gas) is discharged to the exterior of the body. In the lung parenchyma 15, there exists intercellular matrix which is elastic. At the time of extension of the lung parenchyma 15, the intercellular matrix is elastically deformed, thereby promoting the extension of the lung parenchyma 15. If the extension of the lung parenchyma 15 is restrained, the function of gas exchange by the lung parenchyma 15 would be lowered, and inflow of the gas into the lung parenchyma 15 would be restrained. On the other hand, the gas having been stagnating in the lung parenchyma 15 is gradually discharged from the lung 10, with the lowering of the gas exchange function of the lung parenchyma 15.

When gas flows into the lung 10, the lung 10 is so deformed as to expand the lung 10 as a whole through dilation on the verge side primarily. Therefore, when the extension of the lung parenchyma 15 present in the vicinity of the verge 11 of the lung 10 are restrained, as shown in FIG. 4B, the expansion of the lung 10 can thereby be restrained effectively. As a result, the lung volume can be reduced efficiently.

The method for restraining the expansion and contraction of the lung parenchyma 15 may be, for example, a method of forming a reduced-elasticity part 31 where the lung parenchyma 15 has a reduced elasticity. In the treatment method according to this embodiment, the living-body tissue of the verge 11 of the lung 10 is cauterized, whereby the lung parenchyma 15 present in the vicinity of the verge 11 is necrotized, resulting in disappearance of the elasticity. With this reduced-elasticity part 31 thus formed, the expansion and contraction of the lung parenchyma 15 can be restrained at the reduced-elasticity part 31 in a sustained manner.

Incidentally, lung volume reduction can be achieved if the expansion and contraction of the lung parenchyma 15 is restrained more after the treatment than before the treatment. It is noted, however, that when the verge 11 of the lung 10 is, for example, compressed to such an extent that a front surface 22 and a back surface 23 of the lung 10 make contact with each other, as shown in FIG. 4B, the elasticity of the lung parenchyma 15 present in the vicinity of the verge 11 can be made to disappear more reliably. The result is an enhanced therapeutic effect.

Examples of the method for cauterization include a method in which hot air is blown to the verge 11, a method in which steam is blown to the verge 11, a method in which the verge 11 is irradiated with a laser beam, and a method in which a heat generating element is brought into contact with the verge 11.

In addition, examples of the method which can be adopted for forming the lung 10 with the reduced-elasticity part 31 include not only the cauterization method, but also a method in which living-body tissue in the surroundings of the verge 11 is fiberized, a method in which the living-body tissue in the surroundings of the verge 11 is necrotized by cooling, and a method in which a hardening agent or the like is injected into or applied to the verge 11. These methods can be used in combination to form the reduced-elasticity part 31.

The method for fiberizing the living-body tissue is not particularly limited. Examples of the applicable method include methods in which a polycation, a polyanion, a polycation-polyanion compound material, a biodegradable material, an adhesive agent or the like is injected into the living-body tissue, a method in which peripheral vessels are embolized, and a method in which ischemia is caused by localized compression with a clip or the like.

Specific, non-restrictive examples of the hardening agent include flexible polymerization curable materials, two-part cross-linking polymers, adhesives, urethane elastomers, photocurable resins, acrylic resins, and bone cements.

Examples of the method for necrotizing by cooling include methods in which liquid nitrogen, dry ice, cold air or the like is used, and a method in which a heat absorbing element is brought into contact with the verge 11 of the lung 10.

Furthermore, a constraining instrument for constraining the living-body tissue of the lung 10 can be used for restraining the expansion and contraction of the lung parenchyma 15. Examples of the constraining instrument applicable here include clips, staplers, open-close type vessels, sutures, bags, nets, etc. for grasping or holding the living-body tissues in the surroundings of the verge 11 of the lung 10 and thereby restraining the expansion and contraction of the lung parenchyma 15 in the vicinity of the verge 11. The use of such a constrainer ensures that the restraining of the expansion and contraction of the lung parenchyma 15 and removal of the restraint can be carried out in a reversible manner.

Incidentally, the treatment for lung volume reduction can be performed by combined use of the method in which the reduced-elasticity part 31 is formed and the method in which the constraining instrument is used. A method by which a reliable therapeutic effect can be provided or a method by which a smooth treatment can be carried out can be arbitrarily selected according to the part to be treated and/or the condition of the patient.

In FIGS. 5A and 5B, a procedure or treatment for restraining the expansion and contraction of the lung parenchyma 15 present in the vicinity of the verge 11 of the lung 10 is described herein below.

The treatment for restraining the expansion and contraction of the lung parenchyma 15 can be carried out by using, for example, a medical device 100 introduced transbronchially, as shown in FIG. 5A. In the case of forming the above-mentioned reduced-elasticity part 31, the medical device 100 may be, for example, an ablation device, a laser irradiation device, a catheter for applying a predetermined fluid or agent, or the like. In the case of using a constraining instrument, it may be any of the above-mentioned various instruments and the like. The introduction of the medical device 100 can be performed by use of a known access device (e.g., a catheter device, a syringe, etc.) 110 so configured as to permit insertion through a bronchus of a lung. Incidentally, an imaging device such as a flexible endoscope can be used together with the access device 110.

The treatment for restraining the expansion and contraction of the lung parenchyma 15 can also be carried out by using, for example, a medical device 100 introduced from the body surface side, as shown in FIG. 5B. For instance, as shown in FIG. 5B, a predetermined port 120 for providing communication between the exterior of the living body and the vicinity of the verge 11 of the lung 10 may be disposed, whereby the medical device 100 can be introduced through the port 120. At this time, a thoracoscope and a laparoscope and the like may be used together with the medical device 100. When a thoracoscope and the like may be used, a port introduced thoracoscope may be added. In another embodiment of the method in accordance with the instant disclosure, instead of disposition of the port 120, thoracotomy (opening of the chest of the living body) may be conducted, whereby the medical device 100 can be introduced through the opened part of the chest.

Incidentally, the treatment for reduction of lung volume can also be carried out by joint use of some of the method in which the treatment is conducted by use of the medical device 100 introduced transbronchially, the method in which the treatment is performed by use of the medical device 100 introduced from the body surface side, and the method in which the treatment is conducted by use of the medical device 100 passed through the opened chest part. An introduction method promising easier access can be arbitrarily selected, depending on the part to be treated and the kind of the medical device. Furthermore, the treatment may be performed jointly with LVRS (Lung Volume Reduction Surgery). In such a joint use, the respective treatments may be carried out either simultaneously or with a time gap therebetween.

Referring now to FIGS. 1A to 3B, a lung 10 to which the treatment method according to this embodiment has been applied will be described. While an example in which the treatment is performed on a right lung lower lobe will be shown in the following description, an equivalent treatment can be conducted also on a right lung upper lobe or middle lobe or on a left lung upper lobe, lower lobe or accessory lobe. In addition, the treatment can be carried out on the right and left lungs of a single patient or on a plurality of lobes of the lung.

Figure 3A:
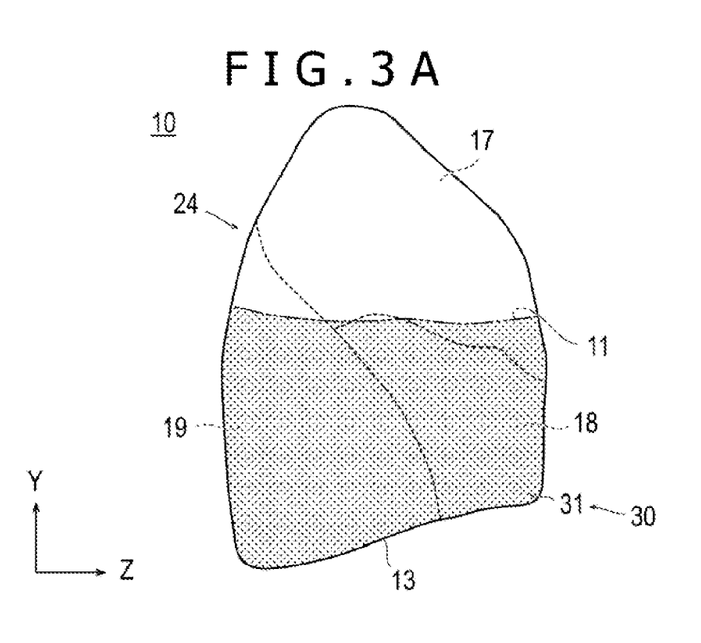
FIG. 3A is a view showing an outside surface of the lung as viewed along arrow 3A in FIG. 1A.
Figure 3B:
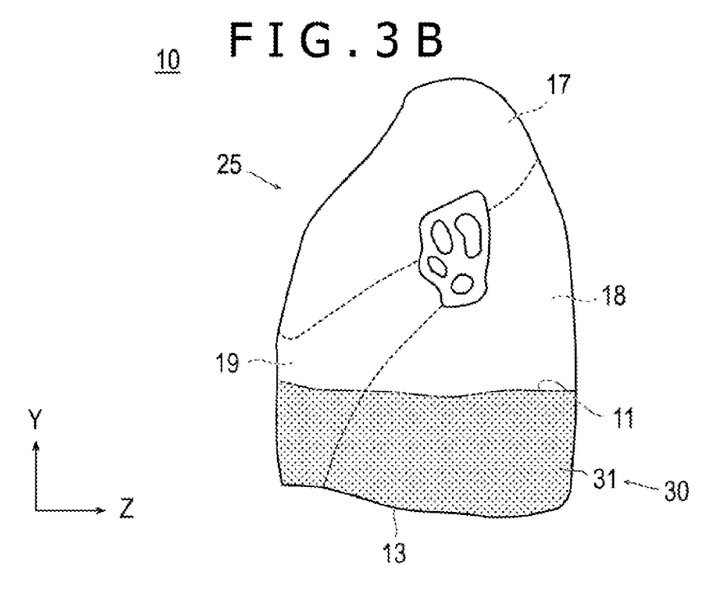
FIG. 3B is a view showing an inside surface of the lung as viewed along arrow 3B in FIG. 1A.

The target part 30 is set at the verge 11 of a bottom surface 21 of a lung 10 (see FIG. 1B), at a front surface 22 of a lung 10 (see FIG. 2A), at a back surface 23 of a lung 10 (see FIG. 2B), at an outside surface 24 of a lung 10 (see FIG. 3A), or at an inside surface 25 of a lung 10 (see FIG. 3B).

Specifically, the treatment is performed on the whole part of the bottom surface 21, on the margo inferior 13 of the front and back surfaces 22 and 23 that is adjacent to the bottom surface 21, and on a predetermined range from the margo inferior 13 of the outside and inside surfaces 24 and 25 that is adjacent to the bottom surface 21. By a process in which the extension of the lung parenchyma 15 are thus restrained in a predetermined range inclusive of the margo inferior 13 of the lung 10, it is possible to restrain a downwardly dilating action of the lung 10 and, hence, to favorably prevent inflow of gas into the inside of the lung 10. In addition, by restraining the expansion and contraction of the lung parenchyma 15 in a continuous region of the predetermined range inclusive of the margo inferior 13, as shown in the drawings, it is possible to restrain more favorably the dilating action of the lung 10. Especially, by conducting the treatment in a condition where the lower part side of the lung 10 is covered in a bag form in a predetermined range inclusive of the bottom surface 21 and the margo inferior 13 continuous with the bottom surface 21, as shown in the drawings, it is possible to restrain vertical dilation of the lung 10 and dilation in the left-right direction of the lung 10 and, hence, to prevent more effectively the inflow of gas into the inside of the lung 10. Incidentally, the restraining of the dilating action of the lung 10 in the above-mentioned manner can be achieved by restraining the expansion and contraction of the lung parenchyma 15 at a predetermined part inclusive of any of the horizontal fissure, oblique fissure, diaphragmatic surface, apex of lung, anterior margin, cardiac notch, and lingula. Therefore, the treatment may be carried out on these parts.

The treatment method according to this embodiment is preferably applied at least to the lobe in which the emphysema-suffering part is formed among the lobes included in the lung 10. By performing the treatment on such a lobe, it is possible to achieve lung volume reduction in a favorable manner. In the example shown in FIGS. 1A to 3B, the treatment is conducted on a lower lobe 19 in which an emphysema-suffering part is formed, among an upper lobe 17, a middle lobe 18, and the lower lobe 19 included in the right lung 10. Incidentally, the treatment is performed on part of the middle lobe 18 adjacent to the lower lobe 19, in addition to the treatment on the lower lobe 19.

As has been described above, according to the treatment method in this embodiment, it is possible to reduce the volume of the lung 10 which has an emphysema-suffering part, thereby alleviating the feeling of difficulty in breathing. In this manner, the treatment method can exhibit a reliable therapeutic effect on chronic obstructive pulmonary disease.

The expansion and contraction of the lung parenchyma 15 is restrained at least at the lobe in which the emphysema-suffering part is formed, of the lobes included in the lung 10. Therefore, lung volume reduction can be achieved more favorably.

In addition, the expansion and contraction of the lung parenchyma 15 is restrained in a predetermined range including at least the margo inferior 13, of the verge 11 of the lung 10. Accordingly, a downward dilating action of the lung 10 can be restrained, so that inflow of gas into the inside of the lung 10 can be prevented suitably.

The expansion and contraction of the lung parenchyma 15 is restrained in a continuous region of the predetermined range inclusive of the margo inferior 13. Therefore, a dilating action of the lung 10 can be restrained further favorably, and reduction of the volume of the lung 10 can be reliably achieved.

Further, the reduced-elasticity part 31 where elasticity of the lung parenchyma 15 is reduced is formed in the lung 10. Therefore, the expansion and contraction of the lung parenchyma 15 can be restrained in a sustained manner.

Since the reduced-elasticity part 31 is formed by cauterizing the living-body tissue of the lung 10, the expansion and contraction of the lung parenchyma 15 can be restrained more reliably.

Since a constraining instrument for constraining the living-body tissue of the lung 10 is used, restraining of the expansion and contraction of the lung parenchyma 15 and removal of the restraint can be carried out in a reversible manner.

In addition, the expansion and contraction of the lung parenchyma 15 are restrained by use of the medical device 100 introduced transbronchially and/or the medical device introduced from the body surface side (inclusive of the medical device 100 introduced through the opened chest part). Therefore, the introduction method promising easier access can be arbitrarily selected, according to the part to be treated and the kind of the medical device. Accordingly, the treatment can be carried out rapidly and easily.

Modifications

Modifications of the part for restraining the expansion and contraction of the lung parenchyma 15 (the target part) will be exemplified below. As has been mentioned above, the volume of the lung 10 can be reduced by applying the treatment method of this embodiment to at least one site of the verge 11 of the lung 10. Therefore, an equivalent effect can be obtained also in the case where the treatment is performed on such a part as shown in each of the following modifications. In the figures, the part surrounded by two-dot chain line represents the verge 11 of the lung 10, and the dotted part indicates the target part 30. In each of the figures, only the back surface 23 of the lung 10 (right lung) is shown for simplification of the description. In regard to each of the bottom surface 21, the front surface 22, the outside and inside surfaces 24 and 25 and the like, however, the target part can be set at the same part as that in the above-described embodiment. Additionally, the target part can also be set at an arbitrary part other than the lower lobe of the lung 10 (right lung). Thus, the target part is not specifically restricted.

Figure 6A:
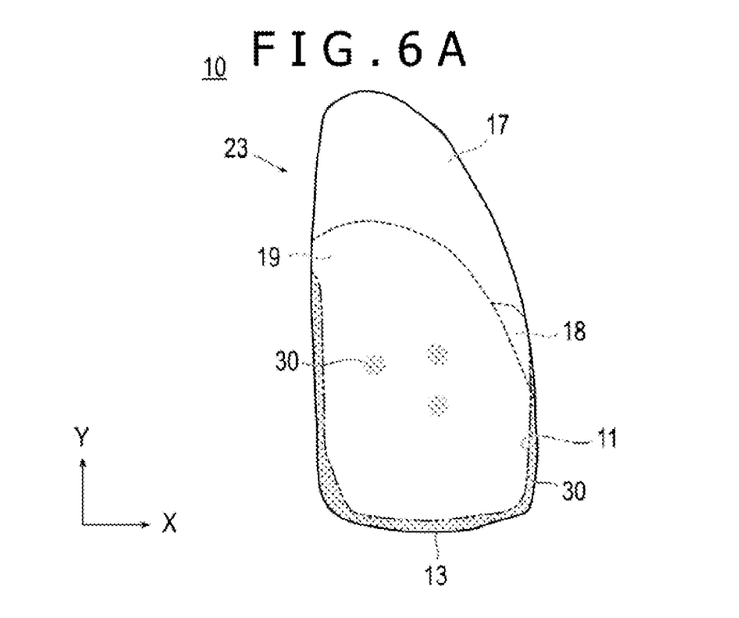
FIGS. 6A and 6B illustrate an example of the part where expansion and contraction of lung parenchyma are restrained.

The treatment can be performed, for example, on the part other than the verge 11, as shown in FIG. 6A. The part other than the verge 11 to be treated, may for example, be a spot-like part. Furthermore, the part other than the verge 11 to be treated may be a plurality of parts. When the treatment is thus performed on the verge 11 and on parts other than the verge 11, the volume of the lung 10 can be reduced efficiently.

Figure 6B:
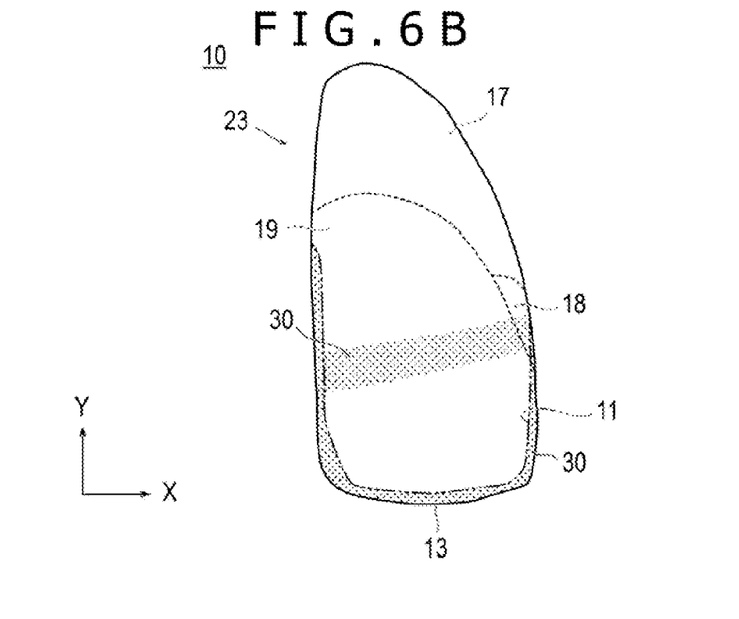

As shown in FIG. 6B, the parts other than the verge 11 can be treated along a linear pattern extending to the verge 11. When the treatment is conducted as shown in this modification, the dilating action of the lung 10 can be restrained also in the direction orthogonal to the front and back surfaces of the lung 10 (in the direction orthogonal to the sheet of paper of the drawing, or the thickness direction of the lung 10). Therefore, the volume of the lung 10 can be reduced more efficiently. Especially, in the case where the front surface 22 is also treated in the same or similar pattern, dilation in the direction orthogonal to the front and back surface can be restrained effectively. While the treatment is conducted along a single linear pattern in this modification, the treatment may be performed along a plurality of linear patterns, whereby dilation can be restrained further effectively.

Figure 7A:
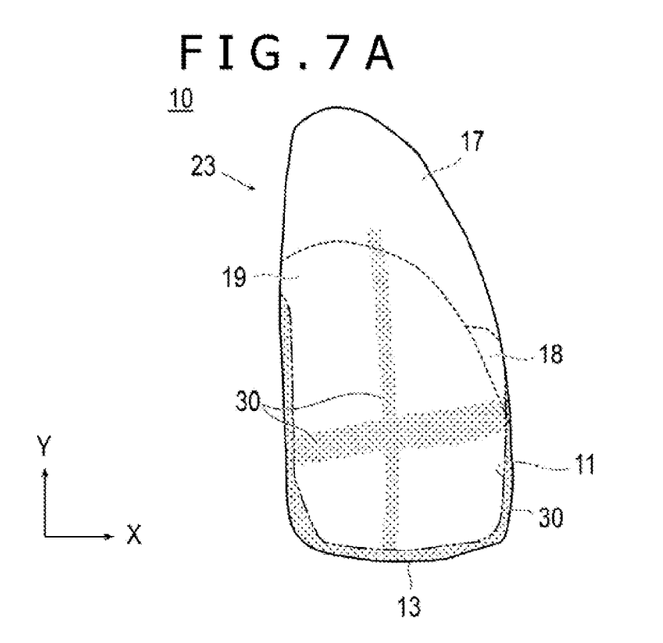
FIGS. 7A and 7B illustrate an example of the part where expansion and contraction of lung parenchyma are restrained.

The treatment can be performed, for example, not only in the pattern shown in FIG. 6B but also in a linear pattern along the extending direction of the lung 10 (in the vertical direction in FIG. 7A), as shown in FIG. 7A. According to this modification, the dilation in the direction orthogonal to the front and back surfaces of the lung 10 can be restrained more effectively than the treatment in the pattern shown in FIG. 6B. While a linear pattern composed of a pair of intersecting lines is shown in FIG. 7A, the treatment may be carried out, for example, in a plurality of linear patterns composed of lines intersecting in a network-like form, whereby the dilation can be restrained further effectively.

Figure 7B:
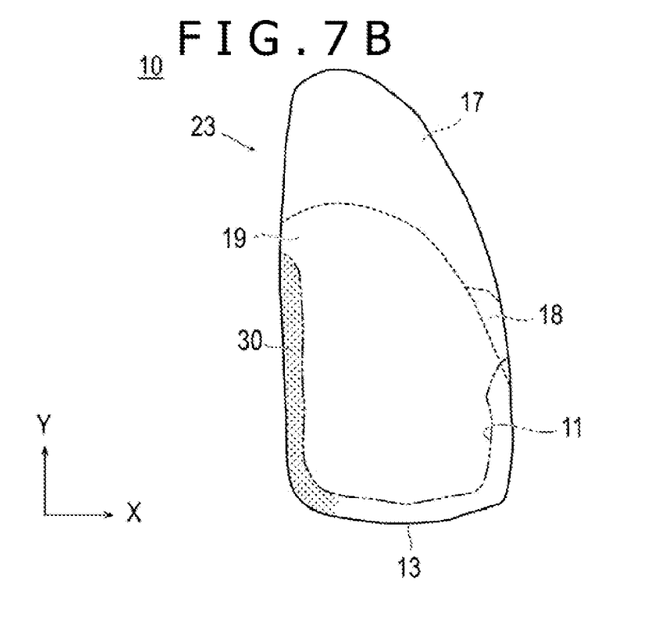

The treatment can be performed, for example, on a continuous region of part of the verge 11, as shown in FIG. 7B. In this case as well, the volume of the lung 10 can be reduced.

Figure 8A:
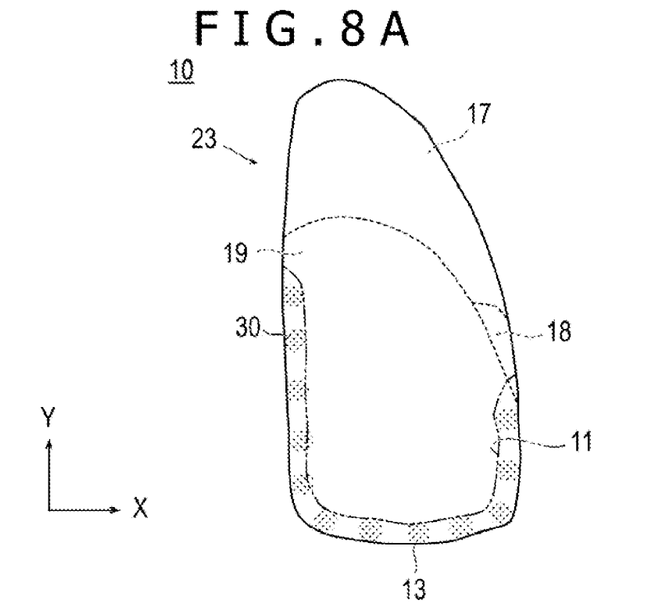
FIGS. 8A and 8B illustrate an example of the part where expansion and contraction of lung parenchyma are restrained.

The verge 11 can also be treated, for example, in a spot-like pattern, as shown in FIG. 8A. The treatment may be performed in a plurality of sites as shown in the figure, or may be performed in a single site. In this case, also, the expansion and contraction of the lung parenchyma 15 are restrained at a plurality of parts in a predetermined range inclusive of the margo inferior 13. Therefore, the dilating action of the lung 10 can be restrained suitably, and the volume of the lung 10 can be reduced reliably.

Figure 8B:
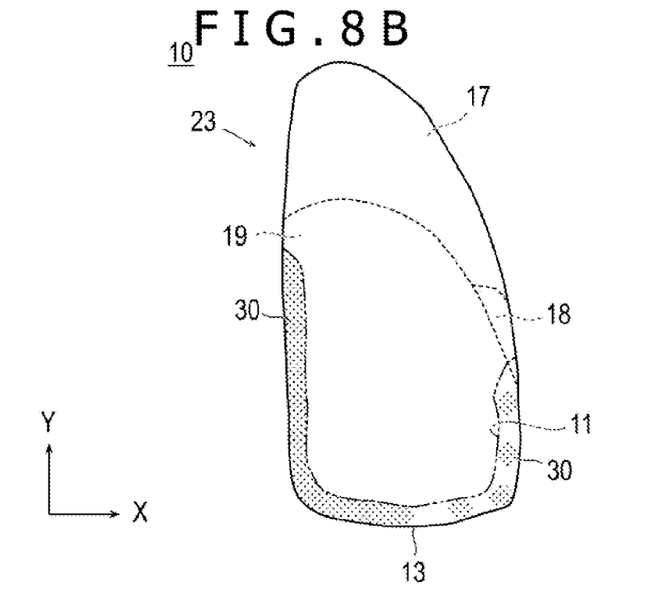

As shown in FIG. 8B, the treatment can also be performed, for example, on a continuous region constituting a part of the verge 11 and, in addition, in a spot-like pattern on other parts of the verge 11. Where the treatment is conducted in this manner, also, the volume of the lung 10 can be reduced.

Example

A working example of the present disclosure will be described herein below.

Figure 9:
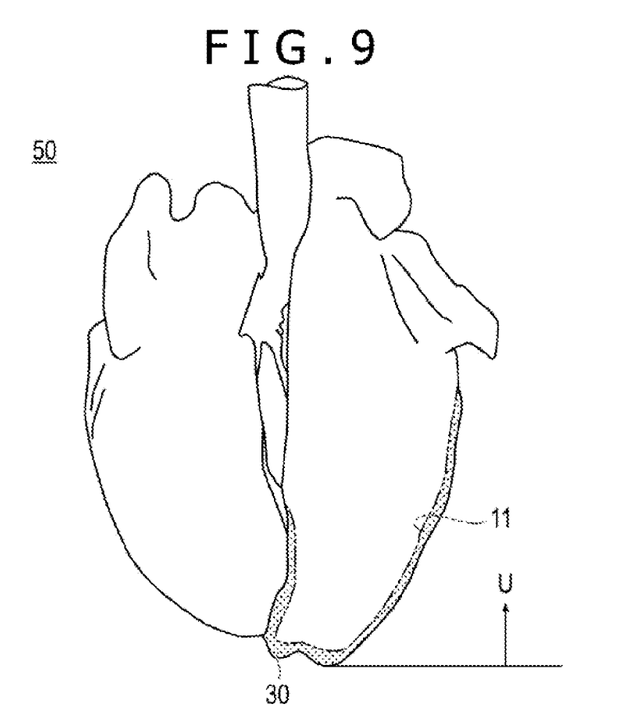
FIG. 9 illustrates working example of the present disclosure, specifically showing a lung wherein expansion and contraction of lung parenchyma present in the vicinity of the verge of the lung are constrained.

FIG. 9 illustrates schematically the result of a treatment performed on a lung 50 isolated from a pig, specifically, on a part similar to the target part 30 shown in FIGS. 1A to 3B. The present disclosure is not, however, limited to the mode described in this Example.

FIG. 9 shows the back side of the isolated lung 50 of the pig. In this Example, hot air at a high temperature was blown to the verge 11 of the surface of the pleura of the right lung 50 of the pig (to the part surrounded by two-dot chain line in the drawing), whereby the tissues and the lung parenchyma 15 in the surroundings of the verge 11 were cauterized. Incidentally, a mask member for prevention of cauterization by the hot air was disposed on other part than the verge 11. After the cauterization, the lung 50 is contained in a predetermined case, the inside of the case was deaerated, and fluid was fed into the inside of the lung 50, thereby dilating the lung 50. In this state, the size of the lung 50 was compared with that before the treatment. It was confirmed that the lung 50 was reduced by the treatment by about 5 cm in the direction of arrow U in FIG. 9. From this result, the lung volume reduction method according to the embodiment was found to be effective.

It should be understood by those skilled in the art that various modifications, combinations, sub-combinations and alterations may occur depending on design requirements and other factors insofar as they are within the scope of the appended claims or the equivalents thereof.

What is claimed is:

1. A method for reduction of lung volume, comprising restraining expansion and contraction of lung parenchyma present in a vicinity of a verge of a lung having an emphysema-suffering part, the restraining performed at least in one site of a pleura at the verge to create a reduced-elasticity part, wherein lung volume is reduced without removal of the emphysema-suffering part, and
wherein the reduced-elasticity part is formed by cauterizing the pleura at the verge of the lung.

2. The method for reduction of lung volume according to claim 1, wherein the restraining of the expansion and contraction of the lung parenchyma is conducted in at least one of margo inferior, horizontal fissure, oblique fissure, diaphragmatic surface, apex of lung, anterior margin, cardiac notch, and lingula, of the verge of the lung.

3. The method for reduction of lung volume according to claim 1, wherein the restraining of the expansion and contraction of the lung parenchyma is conducted at least in a continuous region of the margo inferior, horizontal fissure, oblique fissure, diaphragmatic surface, apex of lung, anterior margin, cardiac notch, and lingula, of the verge of the lung.

4. The method for reduction of lung volume according to claim 1, wherein the restraining of the expansion and contraction of the lung parenchyma is conducted at least at a plurality of the margo inferior, horizontal fissure, oblique fissure, diaphragmatic surface, apex of lung, anterior margin, cardiac notch, and lingula, of the verge of the lung.

5. The method for reduction of lung volume according to claim 1, wherein the restraining of the expansion and contraction of the lung parenchyma is conducted in one or more of a spot-like pattern or in a linear pattern on the pleura at the verge.

6. The method for reduction of lung volume according to claim 1, wherein the restraining of the expansion and contraction of the lung parenchyma is conducted by use of a medical device introduced transbronchially.

7. The method for reduction of lung volume according to claim 1, wherein the restraining of the expansion and contraction of the lung parenchyma is conducted by use of a medical device introduced from an abdomen.

8. The method for reduction of lung volume according to claim 1, wherein no vacuum is applied to the reduced-elasticity part after the living-body tissue is cauterized.

9. The method for reduction of lung volume according to claim 1, wherein the restraining of the expansion and contraction of the lung parenchyma is conducted in a linear pattern.

10. A method for reduction of lung volume by restraining expansion and contraction of lung parenchyma present in a vicinity of a verge of a lung having an emphysema-suffering part comprising
introducing a cauterizing medical device to a pleura of the lung via the abdomen;
cauterizing the pleura at the verge in the area of the emphysema-suffering part to create a reduced-elasticity part, wherein lung volume is reduced without removal of the emphysema-suffering part, and
wherein the pleura is cauterized in a spot-like, linear or cross-shaped pattern on at least one or more of margo inferior, horizontal fissure, oblique fissure, diaphragmatic surface, apex of lung, anterior margin, cardiac notch, and lingula, of the pleura at the verge of the lung;
wherein the cauterizing medical device is a heat generating element, laser or hot air.

11. The method for reduction of lung volume according to claim 10, wherein the cauterization is conducted in a first portion of the pleura using a spot-like pattern and in a second portion of the pleura using a liner pattern.

12. The method for reduction of lung volume according to claim 10, wherein the cauterization is conducted in a cross-like pattern, wherein the cross-like pattern having a first arm extending across the pleura from a first side of the verge to a second side of the verge and a second arm extending across the pleura from a third side of the verge to a fourth side of the verge.

13. A method for reduction of lung volume, comprising
restraining expansion and contraction of lung parenchyma present at a verge of a lung having an emphysema-suffering part, the restraining performed at least in one site of the outer surface of the verge to create a reduced-elasticity part, wherein lung volume is reduced without removal of the emphysema-suffering part, and
wherein the reduced-elasticity part is formed by cauterizing living-body tissue of the lung irradiating the verge with a laser beam or contacting the verge with a heat generating element.

* * * * *